(12) United States Patent
Földes

(10) Patent No.: US 6,843,778 B2
(45) Date of Patent: Jan. 18, 2005

(54) DERMATOLOGICAL METHOD AND DEVICE

(76) Inventor: Gábor Földes, Bagoly u, 145, H-2030 Érd (HU)

( * ) Notice: Subject to any disclaimer, the term of this patent is extended or adjusted under 35 U.S.C. 154(b) by 12 days.

(21) Appl. No.: 10/363,118

(22) PCT Filed: Jul. 18, 2001

(86) PCT No.: PCT/HU01/00081
§ 371 (c)(1),
(2), (4) Date: Feb. 28, 2003

(87) PCT Pub. No.: WO02/09630
PCT Pub. Date: Feb. 7, 2002

(65) Prior Publication Data
US 2004/0039380 A1 Feb. 26, 2004

(30) Foreign Application Priority Data
Jul. 31, 2000 (HU) .......................................... P 0003007

(51) Int. Cl.[7] ................................................ A61F 13/00
(52) U.S. Cl. ............................. 602/2; 128/898; 607/88; 602/41
(58) Field of Search ............... 602/1–41; 604/304–307; 607/88–90; 128/888, 898

(56) References Cited

U.S. PATENT DOCUMENTS

| | | | |
|---|---|---|---|
| 2,524,286 A | 10/1950 | Dreyer | |
| 4,686,986 A | 8/1987 | Fenyö | |
| 4,889,121 A | 12/1989 | Fassina | |
| 4,896,901 A | 1/1990 | Ekelund | |
| 4,917,112 A | 4/1990 | Kalt | |
| 5,000,741 A | 3/1991 | Kalt | |
| 5,001,608 A * | 3/1991 | Kehrli et al. .................. | 362/19 |
| 5,060,662 A * | 10/1991 | Farnswoth, III ............ | 128/888 |
| 5,989,245 A * | 11/1999 | Prescott ........................ | 606/14 |
| 6,587,711 B1 * | 7/2003 | Alfano et al. ................ | 600/476 |

FOREIGN PATENT DOCUMENTS

| | | | | |
|---|---|---|---|---|
| DE | 19544255 | * | 3/1997 | ........... A61F/13/00 |
| EP | 0290875 | * | 4/1988 | ........... B42D/15/02 |

* cited by examiner

Primary Examiner—Roy D. Gibson
Assistant Examiner—Henry M Johnson, III
(74) Attorney, Agent, or Firm—Brooks Kushman P.C.

(57) ABSTRACT

A flexible surgical plaster and an associated dermatological method of use for promoting healing of skin injuries and scars includes a flexible base layer having a window. The base layer is flexibly attachable to skin surface surrounding a skin injury or scar such that the window is flexibly placed above and exposes the skin injury or scar to light when the base layer is attached to the skin surface. The surgical plaster further includes a flexible translucent light-polarizing film placed in the window of the base layer such that the light-polarizing film is flexibly placed above the skin injury or scar when the base layer is attached to the skin surface. The light-polarizing film transforms ambient light received by the light-polarizing film into polarized light and transmits the polarized light through the window to the skin injury or scar when the base layer is attached to the skin.

20 Claims, 2 Drawing Sheets

DERMATOLOGICAL METHOD AND DEVICE

BACKGROUND OF THE INVENTION

1. Field of the Invention

The invention relates to a dermatological method and device to promote healing of injuries and/or scars on the surface of skin, which makes possible simple and efficient treatment of skin surface with polarized light.

2. Background Art

To heal pathological skin affections respectively to promote healing beside the generally applied medicinal treatment it is also a well-known method to heal injuries or scars on the surface of the skin with polarized light, which helps healing by stimulating processes taking place in cells. Practical clinical experiences prove, that application of polarized light, lighting of wounds or scars on the surface of the skin considerably accelerates healing. According to comparative tests treatment with polarized light initiated process of healing even in case of chronic sores of long duration, during which at first sores emptied, secretion decreased, then ceased, capillaries appeared on the sore base, epithelisation started around the edge of the wound and a steady healing started.

According to the prior art HU 186 081 patent description makes known equipment suitable for stimulating biological processes in connection with cell activity, particularly to heal pathological skin affections, sores, ulcers and other injuries of the body with equipment producing linearly polarized light. The equipment has an incoherent source of light emitting light of more than 300 nm wave-length, a polarizator built in or separate, and a light-deflecting system leading the rays to the given direction.

Patent description HU 210 570 makes known a curing lamp emitting polarized light. In the lamp described by the patent there is a housing, a handle built-in the housing and a maximum 100 W electric bulb arranged in the housing. The device has among others a reflector arranged directly behind the bulb, a polarizator placed in the light-beam of the bulb, and a color-filter sheet filtering ultra-violet components from the light emitted.

The disadvantage of the unknown solutions of using polarized light for curing is, that a separate device is needed for lighting the surface of the injury to be cured, and the surface to be cured can be lighted only periodically during treatment sessions. During treatment lighting is of great intensity, but relatively short-term, so the injury is lighted for a relatively short time during relatively short periods of the healing.

An additional disadvantage is, that it is difficult or can hardly be guaranteed in case of the known solutions, that the polarization direction of the light reaching the skin surface is always identical. In case of applying a lamp emitting polarized light the position of the part of the body or the body surface can change even during a single session compared to the lamp, which causes the change of the direction of the polarization direction of the light reaching the skin surface, which may decrease the efficiency of the treatment.

SUMMARY OF THE INVENTION

Working out the solution according to the invention our aim was to make a method and device, which can ensure continuos lighting of the surface of the injury with low-intensity polarized light and can ensure keeping the direction of the polarized light identical during the whole treatment.

We realized, when working out the solution, that if the lighting of the surface of the injury or scar to be healed is carried out with a device put on the skin surface, transforming outside light into polarized light, then the set aim can be achieved.

The object of the invention is a dermatological method to promote healing of injuries and/or scars on the surface of skin, when skin surface treated is lighted with polarized light. Said method is characterized by that a translucent polarizing layer is put above the injury and/or scar to be treated and a multipolar light is let through said translucent polarizing layer from outside and the skin surface is lighted with the polarized light passing through the light-polarizing layer.

The object of the invention further is a dermatological device to promote healing of injuries and/or scars on the surface of skin, realizing preferably the method according to the invention, has a base layer which is known in itself and said base layer fits well to the surface of the skin. The device is characterized by that it has a flexible light-polarizing layer to be placed above the skin surface to be treated and said light-polarizing layer joins a base layer and fits flexibly to the surface of the skin.

In a preferred application of the method according to the invention, the light passing through light-polarizing layer to the skin surface is either linearly polarized or circularly polarized light. A color-filter layer and/or light-filtering layer is applied below and/or above polaring layer and the wavelength of the light getting to the skin surface is in the range of the visible light, it is preferably blue, or purple, or red, or orange. The lighting of the skin surface takes place continuously or periodically during the treatment.

In another preferred application of the method according to the invention the multipolar light applied is a natural light, preferably sunlight. The multipolar light is artificial light, in given case the light of electric bulbs, or neon, or mercury-arc tube or laser.

In a further preferred application of the method according to the invention, medicine or a curative product is placed before or at the same time of the placement of the light-polarizing layer on the skin surface to be treated.

In a preferred embodiment of the dermatological device according to the invention, the device has a flexible base layer joining the surface of the skin which is known in itself, and the surface of the device fitting to the skin surface is provided preferably with a self-adhesive layer and further the light-polarizing layer is a flexible polar film.

In another preferred embodiment of the dermatological device according to the invention, the device is formed as a surgical plaster with a skin-friendly base layer and a skin-friendly adhesive layer which are known in themselves and the light-polarizing layer of said surgical plaster is shaped from a translucent polarizing film placed in a window formed on the base layer. The light-polarizing layer is either linearly polarized or circularly polarized light-polarizer.

In a further preferred embodiment of the dermatological device according to the invention, one or more light-filter layer, preferably color-filter or light-intensity filter, in given case ultraviolet-filter and/or infrared filter, is placed below or above the light polarizing layer, said color-filter or light-intensity filter, in given case ultraviolet-filter and/or infrared filter are preferably made of flexible films. The base layer and/or the light-polarizing layer and/or the color-filter layer is provided with perforation.

In a further preferred embodiment of the dermatological device according to the invention, the part of the device joining the skin contains medicine or a curative product.

We will present the method according to the invention with the following examples of application:

EXAMPLE 1

One of the main fields of application of the method according to the invention is treating the skin surface with light of great intensity, appropriate occasional illumination. It can be applied in case of skin surfaces, which require intensive treatment and are situated on a part of the body which is covered by clothes, therefore outside natural light can not reach them. The duration of treatment is preferably 3–5 minutes, the applied intensity is 4 . . . 10 W/square meter. The wavelength of the applied light is 400 . . . 450 nm (blue), or 700 . . . 750 nm (red).

EXAMPLE 2

Another main field of application of the method according to the invention is, when the skin surface is spontaneously lighted with relatively low-intensity light, preferably from a natural or artificial light source coming from the outer surroundings. It is especially appropriate, when the surfaces to be treated are on parts of the body where they are not regularly covered by clothes, so they are effected by sunlight or artificial lighting. This solution can be advantageously applied in case of skin surfaces not requiring intensive treatment, for examples warts, spots, scars. The duration of the lighting is continuous, respectively dependent on outer lighting. This way long-term treatment is possible, which for example in the case of a polar-film placed as a surgical plaster require no special arrangement.

In case of treatment with spontaneous outer light the intensity of the curing light can range from a few tenth W/square meter upto a few W/square metre. To prevent adverse effects of beaming sunlight we can preferably apply a light-filtering layer. We can choose the color required according to the clinical experiences from the spectrum of the outer light with an appropriately applied color-filter.

BRIEF DESCRIPTION OF THE DRAWINGS

The solution according to the invention will be described further with the help of the enclosed figures.

DETAILED DESCRIPTION OF THE PREFERRED EMBODIMENT(S)

Figure 1:
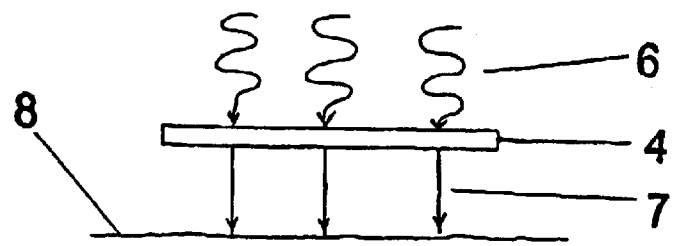
FIG. 1 shows the principle of the method of the device according to the invention.

FIG. 1 shows the principle of the method of the device according to the invention. In the base case the incoming outer multipolar light 6 gets to the light-polarizing layer 4, which produces linearly polarized light 7. This polarized light 7 gets to the skin surface 8.

Figure 2:
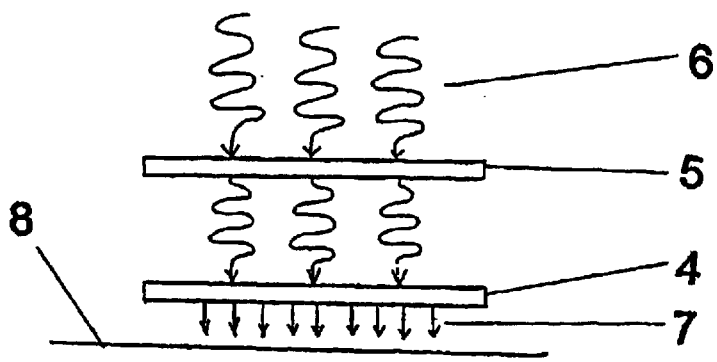
FIG. 2 shows the mode of the operation of the device according to the invention in case of a preferred embodiment.

FIG. 2 shows the mode of the operation of the device according to the invention in case of a preferred embodiment. This case the outer light 6 goes through first the light-filtering layer 5, then it gets to the light-polarizing layer 4, and from there it proceeds as linearly polarized light 7 to the skin surface 8 to be treated. The light-filtering layer 5 is preferably a color-filter, or ultraviolet-filter, which ensures the choosing of the required color, or the filtering of the harmful radiation, for example the filtering of the ultraviolet radiation.

Figure 3:
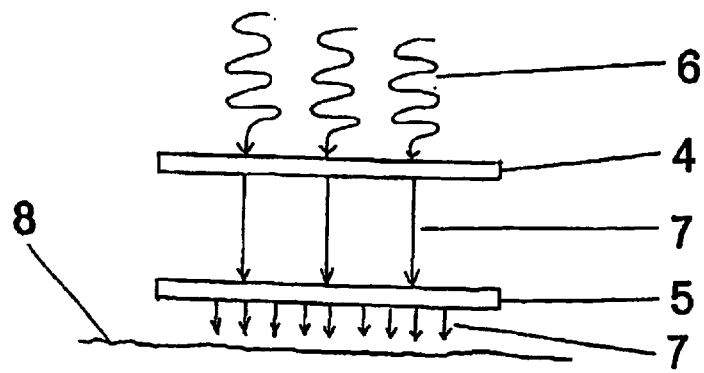
FIG. 3 shows the mode of the operation of the device according to the invention in case of another preferred embodiment.

FIG. 3 shows the mode of operation of the device according to the invention in case of another preferred embodiment. This case the outer multipolar light 6 first gets to the light-polarizing layer 4 and proceeds from there as polarized light 7 through the light-filter layer 5 to the skin surface 8 to be cured. The light-filter layer 5 will help choose the required color from the polarized light 7, respectively filter the harmful radiation, for example ultraviolet radiation.

Figure 4:
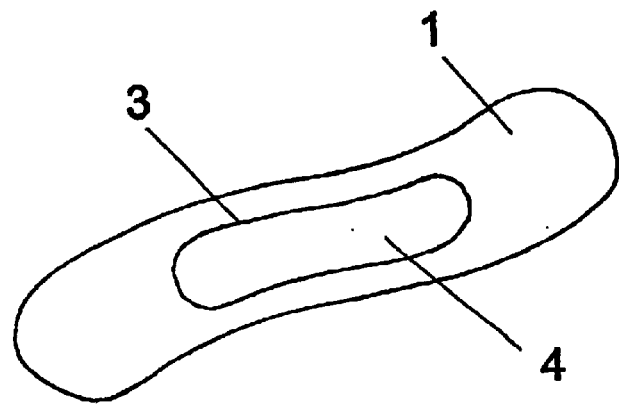
FIG. 4 shows a preferred embodiment of the device according to the invention in case of a definite realization as a surgical plaster in elevation.

FIG. 4 shows a preferred embodiment of the device according to the invention in case of a definite realization as a surgical plaster in elevation. The base layer 1 of the device can be seen in the figure. The light-polarizing layer 4 as a film is placed in the window 3 of the base layer 1. The device has a preferably skin-friendly self-adhesive layer 2 providing an easy way of placing said self-adhesive layer 2 on the skin surface 8 to be treated. The device formed this way as a surgical plaster polarizes the natural light, and the light gets to the skin in an always identically polarized way.

Figure 5:
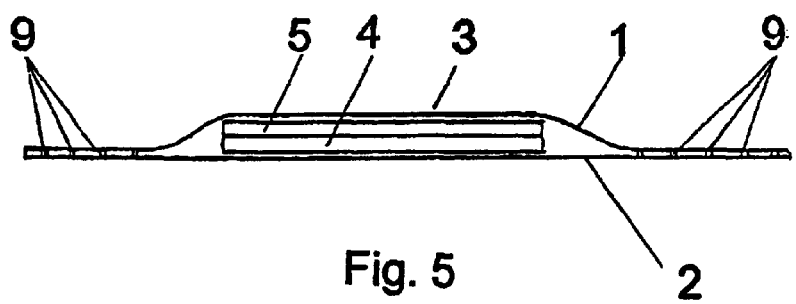
FIG. 5 shows a preferred embodiment of the device according to the invention in section.

FIG. 5 shows a preferred embodiment of the device according to the invention in section. As it can be seen in the figure, there is a self-adhesive layer 2 below the base layer 1 ensuring self-adhesive fixing to the skin. The light-polarizing layer 4 and the light-filtering layer 5 arranged above it can be seen in the lower part of the window 3 of the device. In case of preferred embodiment seen in the figure the base layer 1 is provided with perforation 9 ensuring airing of the skin.

Figure 6:
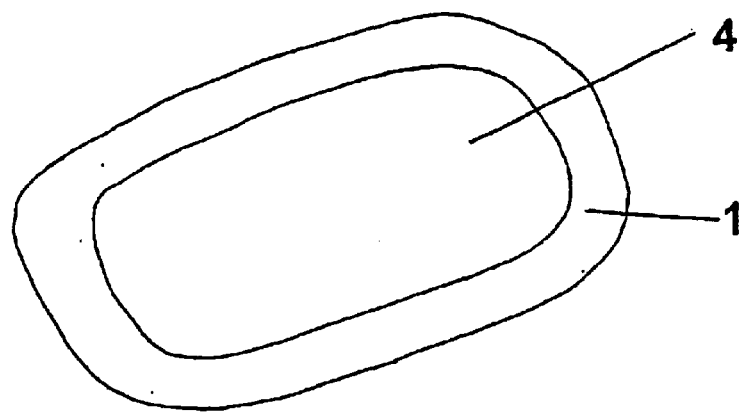
FIG. 6 shows a preferred embodiment of the device according to the invention applied as covering film of injuries on a bigger skin surface in elevation.

FIG. 6 shows a preferred embodiment of the device according to the invention applied as covering foil of injuries on a bigger skin surface in elevation. In case of this preferred embodiment the base layer 1 is placed at the edge of the device and encloses the light-polarizing layer 4 inside. Fixing to the skin takes place preferably with the self-adhesive layer 2 on the back of the base layer 1 as described above.

In a possible preferred embodiment of the solution according to the invention, the device is made of skin-friendly materials, which are suitable for keeping near the skin for longer duration. The base layer 1 or in given case the polarizing layer 4 applied as film or foil is provided with perforation 9. Therefore the device is of porous structure, ensuring airing and can be applied as a scar-covering film. The shape of the device is in given case corresponds with the shape of the part of the body or skin surface to be treated.

The colors preferably applied during treatment are purple with curative effect, blue with antiseptic effect. These colors can be applied in the color-filter film in the device according to the invention for various definite preferred embodiments. In case the skin surface gets light continuously the efficiency of the polarizing film is not critical, it is not necessary to use a thick film. UV-filter is advantageous to prevent undesired UV effects.

During the treatment and for the lighting of the device according to the invention mainly only multipolar sources of light should be used and the device emitting polarized light is not or only to a lesser extent suitable. Due to the possibly different polarization, the skin surface might not get light, because the polarizing layer does not let polarized light of different character through. The direction of polarization of the polarizing layer 4 is indicated with arrows on the finished product, it makes possible to always place the device on the skin surface to be treated with the appropriate polarization direction.

The advantage of the solution according to the invention is, that it promotes healing of injuries without scars, respectively eliminating scars. It can be further advantageously applied in the field of cosmetic preparations, to diminish inflammations, healing of plastic surgery scar-free, unwrinkling. The device according to the invention ensures continuously the identical polarization level during the treatment. In case of use of a source of light of appropriately, large light-intensity light the method and device according to the invention can be used for the stimulation and healing of tissues, for example muscle tissue, connecting tissue, cartilage, and bone situated 4–6 centimeters below the skin surface.

What is claimed is:

1. A dermatological method for promoting healing of skin injuries and scars, the dermatological method comprising:

providing a flexible surgical plaster having a base layer and a flexible translucent light-polarizing foil, the base layer having a window and the light-polarizing foil being placed in the window;

attaching the base layer to skin surface surrounding a skin injury or scar such that the window and the light-polarizing foil are flexibly and substantially permanently placed onto the skin surface above the skin injury or scar with the window exposing the skin injury or scar to light from the light-polarizing foil;

exposing the light-polarizing foil to ambient light;

using the light-polarizing foil to transform the ambient light into polarized light; and using the light-polarizing foil to transmit the polarized light through the window to the skin injury or scar in order to promote healing of the skin injury or scar.

2. Method according to claim 1 wherein:

using the light-polarizing foil to transform the ambient light into polarized light includes using the light-polarizing foil to transform the ambient light into either linearly polarized light or circularly polarized light.

3. Method according to claim 1 further comprising:

applying a light-filter layer below and/or above the light-polarizing foil such that the polarized light reaching the skin injury or scar has a wave-length in the range of visible light.

4. Method according to claim 1 wherein:

exposing the light-polarizing foil to ambient light takes place continuously or periodically such that the light-polarizing foil correspondingly transmits polarized light through the window to the skin injury or scar continuously or periodically.

5. Method according to claim 1 wherein:

the ambient light is sunlight.

6. Method according to claim 1 wherein:

the ambient light is artificial light.

7. Method according to claim 6 wherein:

the artificial ambient light is from a light bulb.

8. Method according to claim 1 further comprising:

placing medicine or a curative product on the skin surface before or at the same time of the placement of the light-polarizing foil above the skin surface.

9. Method according to claim 1 further comprising:

applying a color-filter layer below and/or above the light-polarizing foil such that the polarized light reaching the skin injury or scar has a color of at least one of blue, purple, red, and orange.

10. A flexible surgical plaster for promoting healing of skin injuries and scars, the surgical plaster comprising:

a flexible base layer having a window, the base layer being flexibly attachable to skin surface surrounding a skin injury or scar such that the window is flexibly and substantially permanently placed onto the skin surface above the skin injury or scar and exposes the skin injury or scar to light when the base layer is attached to the skin surface; and a flexible translucent light-polarizing foil placed in the window of the base layer such that the light-polarizing foil is flexibly and substantially permanently placed onto the skin surface above the skin injury or scar when the base layer is attached to the skin surface, wherein the light-polarizing foil transforms ambient light received by the light-polarizing foil into polarized light and transmits the polarized light through the window to the skin injury or scar in order to promote healing of the skin injury or scar when the base layer is attached to the skin.

11. The surgical plaster according to claim 10 wherein:

the base layer further includes a self-adhesive layer for flexibly attaching the base layer to the skin surface.

12. The surgical plaster according to claim 11 wherein:

the base layer and the self-adhesive layer are skin-friendly.

13. The surgical plaster according to claim 10 wherein:

the light-polarizing foil is either linearly polarized for transforming ambient light into linearly polarized light or circularly polarized for transforming ambient light into circularly polarized light.

14. The surgical plaster according to claim 10 further comprising:

at least one light-filter layer placed below or above the light-polarizing foil in the window of the base layer.

15. The surgical plaster according to claim 14 wherein:

the at least one light-filter layer includes a light color filter.

16. The surgical plaster according to claim 14 wherein:

the at least one light-filter layer includes a light intensity filter.

17. The surgical plaster according to claim 14 wherein:

the at least one light-filter layer includes an ultraviolet filter.

18. The surgical plaster according to claim 14 wherein:

the at least one light-filter layer includes an infrared filter.

19. The surgical plaster according to claim 10 wherein:

the base layer includes perforations.

20. The surgical plaster according to claim 10 wherein:

the base layer contains medicine or a curative product.

* * * * *